US00PP08303P

United States Patent [19]

Vletter

[11] Patent Number: Plant 8,303

[45] Date of Patent: Jul. 13, 1993

[54] LILY PLANT NAMED MEDITERRANNEE

[75] Inventor: Floris Vletter, Rijnsburg, Netherlands

[73] Assignee: Gebr. Vletter & J.A. Den Haan, Rijnsburg, Netherlands

[21] Appl. No.: 796,530

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Mediterrannee, characterized by its medium pink base flower color, with lighter pink near the edges and a darker red-purple near the base and midvein, downwardly reflexing flower tips, relatively long stems, and its floriferous habit.

1 Drawing Sheet

The present invention comprises a new and distinct cultivar of lily, botanically known as Lilium, commercially known as Lilium oriental hybrid, and hereinafter referred to by the cultivar name Mediterrannee. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the primary objective of creating new lily cultivars having intense purple flower color, while at the same time retaining other traits necessary or desirable for cut flower production.

The new cultivar was originated from a hybridization made by the inventor in a controlled breeding program in Rijnsburg, The Netherlands in 1981. Both the male and female parents were unnamed seedlings.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for Mediterrannee are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Base flower color is medium pink, with a much lighter pink toward the edges, and a substantially darker red-purple near the base and along the midvein;
2. Tips of flowers reflex strongly downwardly;

3. Floriferous habit.

The accompanying photographic drawing shows typical flower characteristics of the new cultivar, with colors being as true as possible with illustrations of this type. The photograph comprises a front perspective view showing fully and partially open flowers and buds at various stages. When flowering is forced under natural light, Mediterrannee produces an inflorescence approximately 9 days earlier than Stargazer, under the same growing conditions. Mediterrannee is fertile.

In the following description, color references are made to The Royal Horticultural Society (R.H.S.) Color Chart. The color values were determined at Wageningen in 1988 and at Rijnsburg in July 1991.

Origin: Seedling from Breeding Program.

Parentage:

*Seed parent.*—Unnamed seedling.

*Pollen parent.*—Unnamed seedling.

Classification:

*Botanical.*—Lilium.

*Commercial.*—Oriental hybrid.

THE PLANT

Form: A single stem carrying numerous pedicels alternately arranged.

Height: Medium to tall; 120 cm at time of opening of anthers of first flower.

Growth habit: Vigorous.

Stem: Circular in transverse section; light green 144B with anthocyanin pigmentation present; internodium length uniform.

Foliage:

*Quantity.*—35–45 leaves depending on growing conditions.

*Size of leaf.*—Mature leaves are short to medium in length (13 cm), and narrow to medium in width (3 cm).

*Shape of leaves.*—Generally ovate.

*Texture.*—Smooth with very weak glossiness; no pubescence.

*Color.*—Medium green 137A.

Bulbs:

*Size.*—Outlet 6–30 cm.

*Color.*—Yellow.

Roots: Both stem and contractile present.

THE BUD

Form: Tapering (like a lancet).
Size: 9–10 cm.
Opening: Unfolds normally.
Color: White with pink shade 62C.
Tepals: Folded, three visible.

THE FLOWER

Blooming habit: Raceme.
Size: 16 cm in total diameter, depending on growing conditions.
Borne: Horizontal.
Shape: Generally in form of hexagonal star; bowl-shaped in cross-section.
Tepalage:
*Number of tepals.*—Six.
*Arrangement.*—Three inner and three outer; some marginal undulation; inner unusually broad compared to outer.
*Color.*—Upper surface: Light purple 62B-C but lighter towards edges, particularly away from base; much darker midvein, purple-red 60A. Lower surface: 62B-C and 60A, similar to upper surface.
*Spotting or marking.*—Purple-red spots 60A, each being approximately 1 mm in diameter and concentrated in the lower portion of tepal.

Nectaries and papillae: Present
Pedicel:
*Length.*—5 cm.
*Color.*—Light green.
*Form.*—Scarcely curved.
Texture: Papillose.
Disease resistance: No disease problems noted to date.
Fragrance: Present; weak.
Lasting quality: Excellent.

REPRODUCTIVE ORGANS

Stamens, anthers:
*Arrangement.*—Anthers form a generally circular pattern.
*Length.*—Short to medium, 8 cm.
*Number.*—Six.
*Filaments.*—White, top light green.
Pollen color: Orange brown.
Anther color: Red brown.
Pistils: One with light green style; top green; length 10 cm.
Stigma: Triangular; purple to dark purple stigma.
Ovaries: Triangular in shape other characteristics typical of oriented lily varieties.

I claim:

1. A new and distinct cultivar of lily plant named Mediterrannee, as illustrated and described.

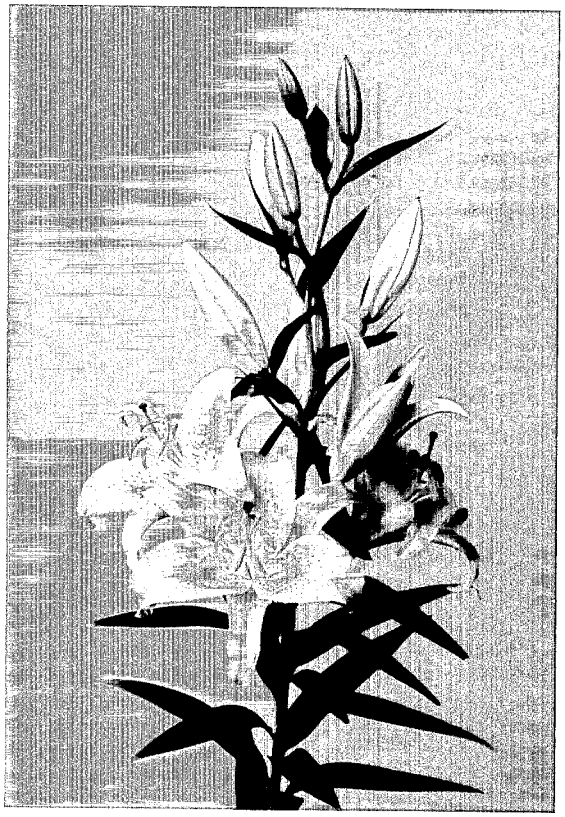

* * * * *